(12) United States Patent
Dickerson et al.

(10) Patent No.: US 6,720,332 B2
(45) Date of Patent: Apr. 13, 2004

(54) OXINDOLE DERIVATIVES

(75) Inventors: Scott Howard Dickerson, Durham, NC (US); David Harold Drewry, Durham, NC (US); James Andrew Linn, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/362,744

(22) PCT Filed: Jun. 28, 2001

(86) PCT No.: PCT/US01/20703
§ 371 (c)(1), (2), (4) Date: Feb. 27, 2003

(87) PCT Pub. No.: WO02/20524
PCT Pub. Date: Mar. 14, 2002

(65) Prior Publication Data
US 2003/0195189 A1 Oct. 16, 2003

Related U.S. Application Data
(60) Provisional application No. 60/230,241, filed on Sep. 1, 2000.

(51) Int. Cl.[7] ................................................ A61K 31/44
(52) U.S. Cl. ............... 514/292; 514/232.8; 514/253.03; 546/84; 544/165; 544/361
(58) Field of Search ........................... 546/84; 544/165, 544/361; 514/292, 253.03, 232.8

(56) References Cited
FOREIGN PATENT DOCUMENTS

| WO | 99/10325 | 3/1999 |
|---|---|---|
| WO | 99/15500 | 4/1999 |
| WO | 00/56710 | 9/2000 |

*Primary Examiner*—Amelia Owens
(74) *Attorney, Agent, or Firm*—John L. Lemanowicz

(57) ABSTRACT

Oxindole derivatives, specifically pyrrolo[3,2-f]quinoline-2-ones, which are useful as CDK4 inhibitors are described herein. The described invention also includes methods of making such oxindole derivatives as well as methods of using the same in the treatment of hyperproliferative diseases.

20 Claims, No Drawings

OXINDOLE DERIVATIVES

This application is filed in pursuant to 35 U.S.C. §371 as a United States National Phase Application of International Application No. PCT/US01/20703 filed Jun. 28, 2001, which claims priority from 60/230,241 filed Sep. 1, 2000.

BACKGROUND OF THE INVENTION

The present invention relates to oxindole derivatives, methods for the preparation of such oxindoles, and use of such oxindoles in the treatment of certain diseases or conditions. In particular, the present invention relates to oxindole derivatives useful as cyclin dependent kinase inhibitors and use of the oxindoles in the treatment of disorders mediated by inappropriate cyclin dependent kinase activity.

Protein kinases catalyze the phosphorylation of various residues in proteins including proteins involved in the regulation of cell growth and differentiation. Cell growth, differentiation, metabolism and function are extremely tightly controlled in higher eukaryotes. The ability of a cell to rapidly and appropriately respond to the array of external and internal signals it continually receives is of critical importance in maintaining a balance between these processes (Rozengurt, Current Opinion in Cell Biology 1992, 4, 161–5; Wilks, Progress in Growth Factor Research 1990, 2, 97–111). The loss of control over cellular regulation can often lead to aberrant cell function or death, often resulting in a disease state in the parent organism. Protein kinases play a critical role in the control of cell growth and differentiation and are key mediators of cellular signals leading to the production of growth factors and cytokines. See, for example, Schlessinger and Ullrich, Neuron 1992, 9, 383. Examples of such kinases include abl, ATK, bcr-abl, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, JNK, KDR, Lck, Lyn, MEK, p38, PDGFR, PIK, PKC, PYK2, tie1, tie2, TRK, UL97, VEGF-R1, VEGF-R2, Yes and Zap70.

Inappropriate protein kinase activity has been associated with a wide variety of disease states and accordingly such kinases have been identified as targets in the treatment of the same. For instance, protein kinases have been implicated as targets in central nervous system disorders such as Alzheimer's (Mandelkow, E. M. et al. FEBS Lett. 1992, 314, 315. Sengupta, A. et al. Mol. Cell. Biochem. 1997, 167,99), pain sensation (Yashlpal, K. J. Neurosci. 1995, 15, 3263–72), inflammatory disorders such as arthritis (Badger, J. Pharm. Exp. Ther. 1996, 279, 1453), psoriasis (Dvir, et al, J. Cell Biol. 1991, 113, 857), bone diseases such as osteoporosis (Tanaka et al, Nature, 1996, 383, 528), cancer (Hunter and Pines, Cell 1994, 79, 573), atherosclerosis (Hajjar and Pomerantz, FASEB J. 1992, 6, 2933), thrombosis (Salari, FEBS 1990, 263, 104), metabolic disorders such as diabetes (Borthwick, A. C. et al. Biochem. Biophys. Res. Commun. 1995, 210, 738), blood vessel proliferative disorders such as angiogenesis (Strawn et al Cancer Res. 1996, 56, 3540; Jackson et al J. Pharm. Exp. Ther. 1998, 284, 687), restenosis (Buchdunger et al, Proc, Nat. Acad. Sci USA 1991, 92, 2258), autoimimune diseases and transplant rejection (Bolen and Brugge, Ann. Rev. Immunol. 1997, 15, 371) and infectious diseases such as viral (Littler, E. Nature 1992, 358, 160), and fungal infections (Lum, R. T. PCT Int. Appl., WO 9805335 A1 980212).

The signals mediated by protein kinases have also been shown to control growth, death and differentiation in the cell by regulating the processes of the cell cycle (Massague and Roberts, Current Opinion in Cell Biology 1995, 7, 769–72). Progression through the eukaryotic cell cycle is controlled by a family of protein kinases called cyclin dependent kinases (CDKs) and their interaction with a family of proteins termed cyclins (Myerson, et al., EMBO Journal 1992, 11, 2909–17). The coordinate activation and inactivation of different cyclin/CDK complexes is necessary for normal progression through the cell cycle (Pines, Trends in Biochemical Sciences 1993, 18, 195–7; Sherr, Cell 1993, 73, 1059–65). Both the critical G1-S and G2-M transitions are controlled by the activation of different cyclin/CDK activities. In G1, both cyclin D/CDK4 and cyclin E/CDK2 are thought to mediate the onset of S-phase. Controlled progression through the G1 phase of the cell cycle is dependent on the activation of CDK4 by cyclin D. This activation results in the phosphorylation of the retinoblastoma protein (pRb) which then dissociates from its binding partner, E2F. The release of E2F from the inactive pRb-E2F complex allows E2F to regulate the transcription of multiple genes required for DNA synthesis. Under normal physiological conditions the pRb pathway is tightly regulated by proteins ($p16^{INK4A}$, p27, p21) that block the catalytic activity of the CDK4/cyclin D complex. Human genetic evidence supports this $p16^{INK4A}$/CDK4/cyclin D/pRb signal as a tumor suppressor pathway that is frequently de-regulated in many human cancers.

Many mechanisms of de-regulation of pRb have been described. These include gene deletion of the $p16^{INK4A}$ locus and down regulation of $p16^{INK4A}$ gene expression. The $p16^{INK4A}$ protein is a naturally occurring intracellular CDK4 inhibitor that functions as a tumor suppressor gene. An additional mechanism of de-regulation of this pathway is overexpression of cyclin D1, the activation subunit of CDK4. The proposed net effect is an increase in CDK4 activity and hyperphosphorylated pRb.

A method of inhibiting CDK4 activity in a mammal suffering from a susceptible tumor would restore pRb to an active tumor suppressor state. The consequences of restoring pRb function would be to cause cell cycle arrest of normal cells while tumor cells in the mammal would undergo apoptosis. Hypophosphorylated pRb protein positively regulates the apoptotic function of p53 via an interaction with mdm2 (J.-K. Hsieh et al. Molecular Cell 3, 181 1999). Hypophosphorylated pRb prevents mdm2-mediated degradation of p53, resulting in activation of p53 and apoptosis of tumor cells.

A method of inhibiting CDK4 activity would therefore presumably serve to selectively kill human tumors, with wild type Rb status, in which the $p161^{INK4A}$/CDK4/cyclin D/pRb is de-regulated. Administration of an agent capable of selectively inhibiting the activity of CDK4 should provide a treatment of Rb positive human cancers with loss of $p16^{INK4A}$ expression and/or overexpression of cyclin D1 protein and therefore block tumor cell survival.

Antisense constructs to cyclin D1 sensitizes human tumor cells to chemotherapy, suggesting CDK4 activity is needed for tumor cell survival in response to DNA damage. (Korman et al. Cancer Research. 59, 3505 1999). In addition, overexpression of $p16^{INK4A}$ protein sensitizes tumor cells to radiation (X. Y. Fu et al. J Cancer Res Clin Oncol 124, 621 1998).

There is a continuing need in the oncology field for new and more effective treatments for cancer. Because CDK4 may serve as a general activator of cell division and suppress apoptosis of tumor cells, specific inhibitors of CDK4 may provide an effective treatment for cancer and other hyperproliferative disorders. At present, there is an unmet need for small molecule compounds that may be readily synthesized and are potent inhibitors of CDK4/cyclin complexes. The present inventors have now discovered novel oxindole derivative compounds that selectively inhibit the catalytic activity of CDK4/cyclin D and/or CDK2/cyclin E thereby providing new treatment strategies for those afflicted with cancer and other disorders mediated by inappropriate cyclin dependent kinase activity.

SUMMARY OF THE INVENTION

In one aspect of the present invention, there is provided a compound of
Formula I

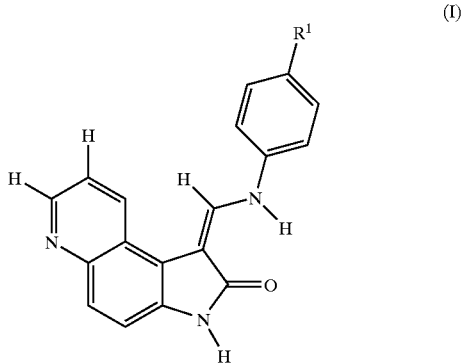

or a salt, solvate, or physiologically functional derivative thereof:
wherein:
$R^1$ is $—(CR^4R^5)_n NR^2R^3$;
n is 1 or 2;
$R^2$ and $R^3$ are independently hydrogen, $C_{1-6}$ alkyl, $C_{1-6}$ alkenyl, $C_{1-6}$ alkoxy-$C_{1-6}$ alkyl, cycloalkyl, heterocyclyl, benzyl, phenyl, napthyl, heteroaryl, heteroaryl-$C_{1-6}$alkyl, or $R^2$ and $R^3$ together with the nitrogen to which they are bound form a 5 or 6 membered heterocyclic or a 5 to 7 membered heteroaryl ring both rings optionally containing 1 or 2 additional oxygen, sulfur, $S(O)_m$, or nitrogen atoms, said 1 or 2 additional nitrogen atoms being optionally substituted by a $C_{1-6}$ alkyl or aryl group;
m is 0, 1, or 2;
$R^4$ and $R^5$ are independently hydrogen or $C_{1-6}$ alkyl; and
wherein any of said $C_{1-6}$ alkyl, $C_{1-6}$ alkenyl, $C_{1-6}$ alkyl-$C_{1-6}$ alkoxy, cycloalkyl, heterocyclyl or heterocyclic, benzyl, phenyl, nalthyl, heteroaryl and heteroaryl-$C_{1-6}$ alkyl groups can be optionally substituted with up to three members selected from a group consisting of halogen, hydroxyl, $—CF_3$ and $—N(CH_3)_2$.

In a second aspect of the present invention, there is provided a pharmaceutical composition including a therapeutically effective amount of a compound of formula I, or a salt, solvate, or a physiologically functional derivative thereof and one or more of pharmaceutically acceptable carriers, diluents and excipients.

In a third aspect of the present invention, there is provided a method of treating a disorder in a mammal, said disorder being mediated by inappropriate CDK4 activity, including: administering to said mammal a therapeutically effective amount of a compound of formula I or a salt, solvate or a physiologically functional derivative thereof.

In a fourth aspect of the present invention, there is provided a compound of formula I, or a salt, solvate, or a physiologically functional derivative thereof for use in therapy.

In a fifth aspect of the present invention, there is provided the use of a compound of formula I, or a salt, solvate, or a physiologically functional derivative thereof in the preparation of a medicament for use in the treatment of a disorder mediated by inappropriate CDK4 activity.

In a sixth aspect of the present invention, there is provided a method of treating a disorder in a mammal, said disorder being mediated by inappropriate CDK4 activity, including: administering to said mammal therapeutically effective amounts of (i) a compound of formula I, or a salt, solvate or physiologically functional derivative thereof and (ii) an agent to inhibit growth factor receptor function.

In a seventh aspect of the present invention, there is provided a method of treating a disorder in a mammal, said disorder being mediated by inappropriate cyclin dependent kinase activity, including: administering to said mammal a therapeutically effective amount of a compound of formula I, or a salt, solvate or physiologically functional derivative thereof.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbon optionally substituted with up to three members selected from a group consisting of halogen, hydroxyl, $—CF_3$ and $—N(CH_3)_2$ and which contains the specified number of carbon atoms. For example, $C_{1-6}$ alkyl means a straight or branched alkyl containing at least 1, and at most 6, carbon atoms. Examples of "alkyl" groups as used herein include, but are not limited to, methyl, ethyl, 2-hydroxyethyl, 2-methoxyethyl, n-butyl, n-pentyl, isobutyl, or isopropyl.

As used herein the term "alkenyl" refers to a straight or branched chain hydrocarbon radical having at least one carbon—carbon double bond, optionally substituted with up to three members selected from a group consisting of halogen, hydroxyl, $—CF_3$ and $—N(CH_3)_2$ and contains the specified number of carbon atoms. For example, $C_{1-6}$ alkenyl means a straight or branched alkenyl containing at least 1, and at most 6, carbon atoms. Examples of "alkenyl" groups include, but are not limited to, ethenyl, propenyl, and butenyl.

As used herein, the term "cycloalkyl" refers to a non-aromatic cyclic hydrocarbon ring having from three to 12 carbon atoms optionally substituted with up to three members selected from a group consisting of halogen, hydroxyl, $—CF_3$ and $—N(CH_3)_2$. "Cycloalkyl" includes, but is not limited to, cyclopropyl, cyclobutyl, cyclopentyl, cyclohexyl, cycloheptyl, or cyclooctyl.

As used herein, the term "heterocyclic" or the term "heterocyclyl" refers to a saturated or partially saturated non-aromatic cyclic hydrocarbon ring system having from three to 12 carbons which also contains at least one heteroatom selected from O, S, or N. The said ring system may optionally be substituted with up to three members selected from a group consisting of halogen, hydroxyl, —CF$_3$ and —N(CH$_3$)$_2$. Examples of "heterocycles" include, but are not limited to, tetrahydrofuran, dihydropyran, tetrahydropyran, pyran, oxetane, thietane, 1,4-dioxane, 1,3-dioxane, 1,3 dioxalane, piperidine, 4-hydroxy-1-piperidine, piperazine, tetrahydropyrimidine, pyrrolidine, morpholinie, thiomorpholine, thiazolidine, oxazolidine, tetrahydrothiopyran, or tetrahydrothiophene.

As used herein, the term "heteroaryl" refers to a monocyclic five to seven-membered aromatic ring, or to a fused bicyclic aromatic ring system comprising two of such monocyclic five to seven membered aromatic rings. These heteroaryl rings contain one or more nitrogen, sulfur, or oxygen heteroatoms, where N-oxides and sulfur oxides and dioxides are permissible heteroatom substitutions and may be optionally substituted with up to three members selected from a group consisting of halogen, hydroxyl, —CF$_3$ and —N(CH$_3$)$_2$. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidinie, quinoline, isoquinoline, benzofuran, benzothiophene, indole, and indazole.

As used herein the term "heteroarylalkyl" refers to a heteroaryl group as described above substituted with an alkyl group containing the specified number of carbon atoms. The "heteroarylalkyl" group may be optionally substituted with up to three members selected from a group consisting of halogen, hydroxyl, —CF$_3$ and —N(CH$_3$)$_2$. An example of a "heteroarylalkyl" as used herein includes, but is not limited to, 4-pyridinylmethyl.

As used herein, the term "alkoxy" refers to the group R$_a$O—, where R$_a$ is alkyl optionally substituted with up to three members selected from a group consisting of halogen, hydroxyl, —CF$_3$ and —N(CH$_3$)$_2$ and contains the specified number of carbon atoms.

As used herein, the term "alkoxyalkyl" refers to the group R$_a$OR$_b$— where Rb is alkyl and R$_a$O is alkoxy as described above optionally substituted with up to three members selected from a group consisting of halogen, hydroxyl, —CF$_3$ and —N(CH$_3$)$_2$ and both of which contain the specified number of carbon atoms.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted.

In one embodiment, R$^2$ and R$^3$ are each C$_{1-6}$alkyl. In a preferred embodiment, R$^2$ is methyl and R$^3$ is methyl, ethyl, propyl, iso-propyl, isobutyl, hydroxyethyl, methoxyethyl, benzyl, or methylpiperidinyl.

In another embodiment, R$^2$ and R$^3$, together with the nitrogen to which they are bound, form a 5 or 6 membered heterocyclic ring, said ring optionally containing 1 or 2 additional nitrogen, C$_{1-6}$ alkyl substituted nitrogen, oxygen, or S(O)$_m$ atoms. In a preferred embodiment, said ring is a piperidine, morphloline or piperazine ring. In an alternate preferred embodiment, R$^2$ and R$^3$ together with the nitrogen to which they are bound form a piperazine ring wherein the additional nitrogen is substituted by a methyl group.

In an another embodiment, R$^2$ and R$^3$ together with the nitrogen to which they are bound form a 5 to 7 membered heteroaryl ring, said ring optionally containing 1 or 2 additional nitrogen, C$_{1-6}$ alkyl substituted nitrogen, oxygen, or S(O)$_m$ atoms. In a preferred embodiment, the ring is an imidazole ring.

In one embodiment, R$^4$ and R$^5$ are independently hydrogen or methyl. In a preferred embodiment, R$^4$ and R$^5$ are each hydrogen.

In another embodiment, R$^2$ and R$^3$ are each C$_{1-6}$ alkyl and R$^4$ and R$^5$ are independently hydrogen or methyl. In a preferred embodiment R$^2$ is methyl; R$^3$ is ethyl, propyl, iso-propyl, isobutyl, hydroxyethyl, methloxyethyl, benzyl, or methylpiperidinyl and R$^4$ and R$^5$ are each hydrogen.

In another embodiment, R$^2$ and R$^3$, together with the nitrogen to which they are bound, form a 5 or 6 membered heterocyclic ring or a 5 to 7 membered heteroaryl ring, optionally containing an additional nitrogen or C$_{1-6}$ alkyl substituted nitrogen, oxygen, or S(O)$_m$ and R$^4$ and R$^5$ are independently hydrogen or methyl. In a preferred embodiment said ring is a piperidine, morpholine or piperazine ring and R$^4$ and R$^5$ are hydrogen. In an alternate preferred embodiment, R$^2$ and R$^3$ together with the nitrogen to which they are bound form a piperazine ring wherein the additional nitrogen is substituted by a methyl group and R$^4$ and R$^5$ are each hydrogen.

In an another embodiment, R$^2$ and R$^3$ together with the nitrogen to which they are bound form a 5 to 7 membered heteroaryl ring, said ring optionally containing 1 or 2 additional nitrogen, $C_{1-6}$ alkyl substituted nitrogen, oxygen, or $S(O)_m$ atoms and $R^4$ and $R^5$ are independently hydrogen or methyl. In a preferred embodiment, the ring is an imidazole ring and $R^4$ and $R^5$ are independently each hydrogen.

Salts of the compounds of the present invention may comprise acid addition salts derived from a nitrogen on a substituent in the compound of formula (I). Salts encompassed within the term "pharmaceutically acceptable salts" refer to non-toxic salts of the compounds of this invention. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

Specific examples of compounds of the present invention include the following:

1-[(Z)-(4-Dimethylaminomethylanilino)methylidene]-1,3-dihydro-2H-pyrrolo[3,2-f]quinoline-2-one;

1-[(Z)-(4-Diethylaminomethylanilino)methylidene]-1,3-dihydro-2H-pyrrolo[3,2-f]quinoline-2-one;

1-[(Z)-(4-(N-Methyl)ethylaminomethylanilino) methylidene]-1,3-dihydro-2H-pyrrolo[3,2-f]quinoline-2-one;

1-[(Z)-(4-(N-Methyl)propylaminomethylanilino) methylidene]-1,3-dihydro-2H-pyrrolo[3,2-f]quinoline-2-one;

1-[(Z)-(4-(N-Methyl)-2-propylaminomethylanilinio) methylidene]1,3-dihydro-2H-pyrrolo[3,2-f]quinoline-2-one;

1-[(Z)-(4-(N-Methyl)-2-methylpropylaminomethylanilino) methylidene]-1,3-dihydro-2H-pyrrolo[3,2-f]quinoline-2-one;

1-[(Z)-(4-(N-Methyl)benzylaminomethylanilino) methlylidene]-1,3-dihydro-2H-pyrrolo[3,2-f]quinoline-2-one;

1-[(Z)-(4-(N-Methyl)-2-hydroxyethylaminomethylanilino) methylidene]-1,3-dihydro-2H-pyrrolo[3,2-f]quinoline-2-one;

1 [(Z)-(4-(N-Methyl)-2-methoxyethylaminomethylanilino) methylidene]-1,3-dihydro-2H-pyrrolo[3,2-f]quinoline-2-one;

1-[(Z)-(4-(4-morpholinyl)methylanilino)methylidene]-1,3-dihydro-2H-pyrrolo[3,2-f]quinoline-2-one;

1-[(Z)-(4-(1-piperidinyl)methylanilino)methylidene]-1,3-dihydro-2H-pyrrolo[3,2-f]quinoline-2-one;

1-[(Z)-(4-(4-hydroxy-1-piperidinyl)methylanilino) methylidene]-1,3-dihydro-2H-pyrrolo[3,2-f]quinoline-2-one;

1-[(Z)-(4-(4-methyl-1-piperazinyl)methylanilino) methylidene]-1,3-dihydro-2H-pyrrolo[3,2-f]quinoline-2-one;

1-[(Z)-(4-(1-imidazoyl)methylanilino)methylidene]-1,3-dihydro-2H-pyrrolo[3,2-f]quinoline-2-one;

1-[(Z)-(4-(N-Methyl)-(1-methyl-4-piperidinyl) aminomethylanilino)methylidene]-1,3-dihydro-2H-pyrrolo[3,2-f]quinoline-2-one; and salts, particularly pharmaceutically acceptable salts, solvates, and physiologically functional derivatives thereof.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing compounds of general formula (I) involves the reaction of a compound of general formula (II)

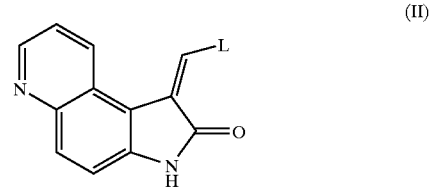

wherein L is a leaving group such as dimethylamino or ethoxy, with compounds of general formula (III)

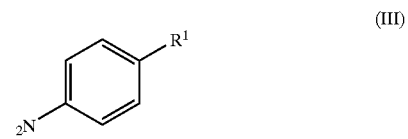

wherein $R^1$ is as defined above.

The general method (A) can be readily carried out by mixing a compound of general formula (II) with a compound of general formula (III) in a suitable solvent, addition of an acid, and optionally heating the mixture. Typically the solvent is a lower alcohol such as methanol, ethanol, 2-propanol and the like, and the acid can be, for example, hydrochloric acid or methanesulfonic acid.

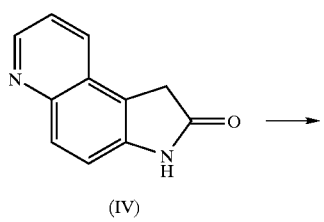

(IV)

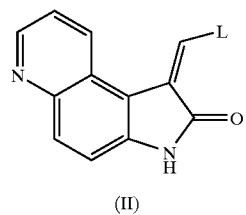

(II)

Compounds of general formula (II) can be obtained by reacting a compound of formula (IV) with a dimethylformamide dialkylacetal, to give compounds of formula (II) wherein L is Me₂N, or with a trialkyl orthoformate or a dialkoxymethylacetate, to give compounds of formula (II) wherein L is an alkoxy group. Conveniently, a dimethylformamide dialkylacetal is dimethylformamide dimethylacetal or dimethylformamide di-tert-butyl acetal and the reaction carried out by mixing the compound of general formula (IV) with the dimethylformamide dialkylacetal and optionally heating the reaction. Preferred trialkyl orthoformates include trimethyl orthoformate and triethyl orthoformate. In a similar manner, diethoxymethyl acetate can be employed to prepare compounds of general formula (II) wherein L is EtO—.

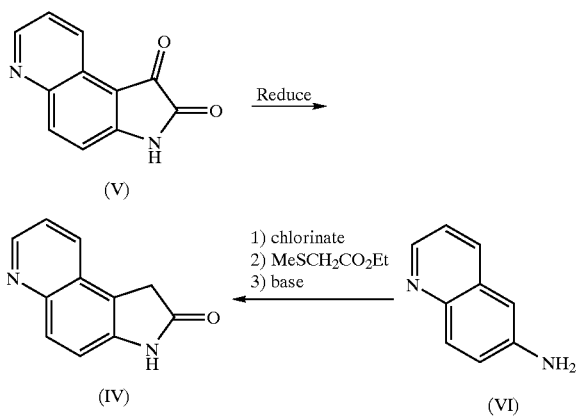

Compounds such as those of formula (IV) can be prepared using procedures described in the literature. Lactams similar to compounds of formula (IV) have been obtained by Wolff-Kischner reduction of carbonyl derivatives such as those of formula (V). Alternatively, compounds of formula (IV) may be obtained by a procedure involving treatment of an amine such as those of formula (VI) with a chlorinating agent followed by ethyl methylthioacetate and a base to give a methylthio derivative. Desulfurization using, for example, activated zinc gives compounds such as those of formula (IV).

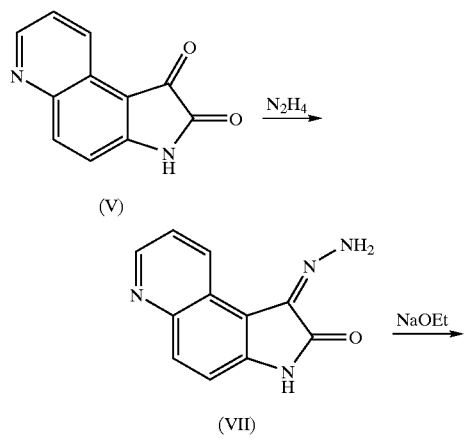

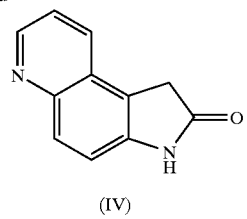

A preferred method involves treating a ketone derivative such as that of formula (V) with hydrazine in an alcoholic solvent such as ethanol and heating the mixture to give a hydrazone such as that of formula (VII). Treatment of a hydrazone such as that of formula (VII) with a base in alcoholic solution and heating the mixture affords the lactam such as that of formula (IV). Typically the base is an alkoxide such as sodium ethoxide and the solvent is ethanol.

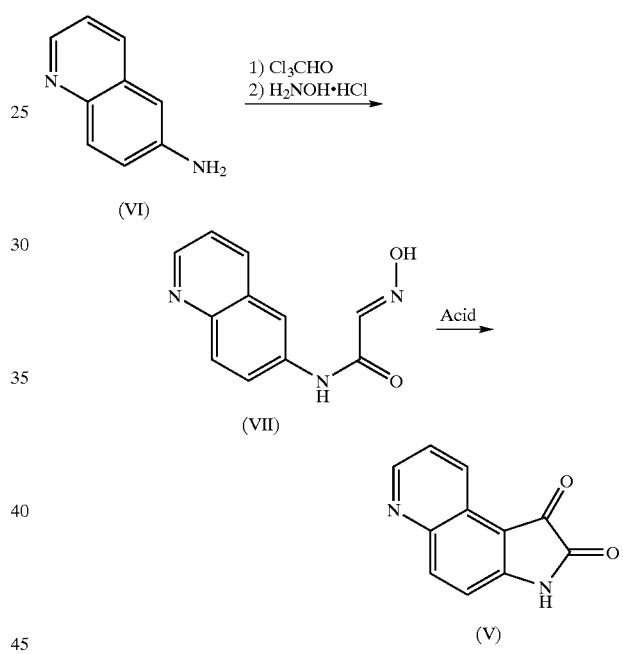

Ketones such as those of formula (V) can be obtained from amines such as those of formula (VI) by a procedure that involves treatment of the amine with chloral followed by hydroxylamine hydrochloride. The resulting hydroxyiminoacetamide of formula (VIII) is then heated in sulfuric acid to give the ketone of formula (V).

The compounds of formula (I) and salts, solvates and physiological functional derivatives thereof, are believed to have anticancer activity as a result of inhibition of the protein kinase CDK4 and their effect on selected cell lines whose growth is dependent on CDK4 protein kinase activity.

The present invention thus also provides compounds of formula (I) and pharmaceutically acceptable salts or solvates thereof, or physiologically functional derivatives thereof, for use in medical therapy, and particularly in the treatment of disorders mediated by inappropriate CDK4 activity.

The inappropriate CDK4 activity referred to herein is any CDK4 activity that deviates from the normal CDK4 activity expected in a particular mammalian subject. Inappropriate CDK4 activity may take the form of, for instance, an abnormal increase in activity, or an aberration in the timing and or control of CDK4 activity. Such inappropriate activity may result then, for example, from overexpression or mutation of the protein kinase leading to inappropriate or uncontrolled activation. Furthermore, it is also understood that unwanted CDK4 activity may reside in an abnormal source, such as a malignancy. That is, the level of CDK4 activity does not have to be abnormal to be considered inappropriate, rather the activity derives from an abnormal source.

The present invention is directed to methods of regulating, modulating, or inhibiting CDK4 for the prevention and/or treatment of disorders related to unregulated CDK4 activity, including cell proliferative disorders, metabolic disorders and excessive cytokine production disorders. The compounds of the present invention can also be used in the treatment of certain forms of cancer, can be used to provide additive or synergistic effects with certain existing cancer chemotherapies, and/or be used to restore effectiveness of certain existing cancer chemotherapies and radiation.

The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy malignant nephrosclerosis, thrombotic microangiopathy syndromes, organ transplant rejection and glomerulopathies. Metabolic disorders include psoriasis, diabetes mellitus, chronic wound healing, inflammation and neurodegenerative diseases.

A further aspect of the invention provides a method of treatment of a mammal suffering from a disorder mediated by inappropriate CDK4 activity, including susceptible malignancies, which includes administering to said subject an effective amount of a compound of formula (I) or a pharmaceutically acceptable salt or solvate thereof, or a physiologically functional derivative thereof. In a preferred embodiment, the disorder is cancer.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof in the preparation of a medicament for the treatment of a disorder characterized by inappropriate CDK4 activity. In a preferred embodiment, the disorder is cancer.

A further aspect of the present invention provides the use of a compound of formula (I), or a pharmaceutically acceptable salt or solvate thereof, or a physiologically functional derivative thereof, in the preparation of a medicament for the treatment of cancer and malignant tumours.

The mammal requiring treatment with a compound of the present invention is typically a human being.

While it is possible that, for use in therapy, therapeutically effective amounts of a compound of formula I, as well as salts, solvates and physiological functional derivatives thereof, may be administered as the raw chemical, it is possible to present the active ingredient as a pharmaceutical composition. Accordingly, the invention further provides pharmaceutical compositions which include therapeutically effective amounts of compounds of the formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I, or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 70 mg to 700 mg, more preferably 5 mg to 100 mg of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar—agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palimitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water-cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as in combination with surgical therapy and radiotherapy. Combination therapies according to the present invention thus comprise the administration of at least one compound of formula (I) or a pharmaceutically acceptable salt or solvate thereof or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula I or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula I or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents include, but are not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methiotrexate, cladrabine, cytarabine, mercaptopurine and thioguanine; and camptothecins such as 9-amino camptothecin, topotecan, irinotecan, CPT-11 and the various optical forms of 7-(4-methylpiperazino-methylene)-10,11-ethylenedioxy-20-camptothecin;

(2) cytotoxic chemotherapeutic agents including, but not limited to, allkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycini, epirubicin, idarubicin, mitomycin-C, dacttinomycin and mithramycin; and platinum coordination complexes such as cisplatin, carboplatin, and oxaliplatin; and (3) other chemotherapeutic agents include, but are not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFr), platelet derived growth factor receptor (PDGFr), vascular endothelial growth factor receptor (VEGFr), and TIE-2; and other tyrosine kinase inhibitors such as inhibitors of CDK2 and CDK4 inhibitors other than those described in the present invention.

In another embodiment, therapeutically effective amounts of the compounds of formula I or salts, solvates or physiologically derived derivatives thereof and agents which inhibit growth factor receptor function may be administered in combination to a mammal for treatment of a disorder mediated by inappropriate CDK4 activity, for instance in the treatment of cancer. Such growth factor receptors include, for example, EGFr, PDGFr, erb-B2, VEGFr, or TIE-2. Growth factor receptors and agents that inhibit growth factor receptor function are described, for instance, in Kath, John C., Exp. Opin. Ther. Patents (2000) 10(6):803–818 and in Shawver et al DDT Vol 2, No. 2 February 1997.

The compounds of the Formula I or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate cyclin dependent kinase activity, including: administering to said mammal a therapeutically effective amount of a compound of formula I, or a salt, solvate or physiologically functional derivative thereof. In one embodiment, the inappropriate cyclin dependent kinase activity is due to at least one of inappropriate CDK2 or CDK4 activity. In another embodiment, the inappropriate cyclin dependent kinase activity is due to inappropriate CDK2 and CDK4 activity. In a further embodiment, the method further includes administering a therapeutically effective amount of a CDK2 inhibitor along with the compounds of formula I or salts, solvates or physiologically functional derivatives thereof. The disorder may be cancer, restenosis, atherosclerosis, inflammatory disease, neurodegenerative disease, viral infection and psoriasis. Preferably the disorder is cancer. Cyclin dependent kinases and inhibitors for the same are described in, for instance, Rosania et al, Exp. Opin. Ther. Patents (2000) 10(2):215–230.

In another aspect of the present invention, there is provided the use of a compound of formula I, or a salt, solvate or physiologically functional derivative thereof in the preparation of a medicament for use in treating a disorder in a mammal, said disorder being mediated by inappropriate cyclin dependent kinase activity. In one embodiment, the inappropriate cyclin dependent kinase activity is due to at least one of inappropriate CDK2 or CDK4 activity. In another embodiment, the inappropriate cyclin dependent kinase activity is due to inappropriate CDK2 and CDK4 activity. In a further embodiment, the use further includes use of a CDK2 inhibitor to prepare said medicament.

The combination of a compound of formula I or salts, solvates, or physiologically functional derivatives with a CDK2 inhibitor may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

Certain embodiments of the present invention will now be illustrated by way of example only. The physical data given for the compounds exemplified is consistent with the assigned structure of those compounds.

EXAMPLES

The following examples are illustrative embodiments of the invention, not limiting the scope of the invention in any way. Reagents are commercially available or are prepared according to procedures in the literature. Example numbers refer to those compounds listed in the tables above. $^1$H NMR spectra were obtained on VARIAN Unity Plus NMR spectrophotometers at 300 or 400 MHz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

Example 1
1-[(Z)-(4-Dimethylaminomethylanilino)methylidene]-1,3-dihydro-2H-pyrrolo[3,2-f]quinoline-2-one

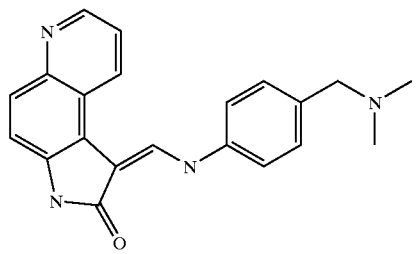

(a) A mixture of dimethylaminomethylidene-1,3-dihydro-2H-pyrrolo[3,2-f]quinoline-2-one (0.1 mmol), 4-dimethylaminomethylaniline (0.1 mmol) and conc. hydrochloric acid (0.02 mL) in ethanol (1 mL) was heated at reflux until the reaction was complete as determined by tlc analysis. The reaction mixture was allowed to cool to room temperature. The solvent was evaporated and the residue purified using silica gel chromatography to give the title compound as an orange-brown solid, 15 mg. (42%). $^1$H NMR (DMSO-d6): δ 2.17 (s, 6H), 3.17 (s, 2H), 7.31–7.51 (m, 6H), 7.74 (d, J=8.7 Hz, 1H), 8.74 (d, J=3.3 Hz, 1H), 8.83 (d, J=6.0 Hz, 1H), 8.86 (d, J=12 Hz, 1H), 10.95 (s, 1H), 11.80 (d, J=12 Hz, 1H); APESI+MS m/z 345 (M+1)$^+$.

b) Dimethylaminomethylidene-1,3-dihydro-2H-pyrrolo[3,2-f]quinoline-2-one

A mixture of 3-H-pyrrolo[3,2-f]quinoline-2-one (13 mmol) and dimethylformamide di-t-butyl acetal (15 mmol) in DMF was stirred at room temperature for 3 h. Ethyl acetate (25 mL) was added and the resulting solid was collected by filtration and allowed to air dry. The desired compound was obtained (70%) and used directly in the next step.

c) 3-H-Pyrrolo[3,2-f]quinoline-2-one

A solution of 2.3 g (12 mmol) of 3-H-pyrrolo[3,2-f]quinoline-1,2-dione and 2.0 ml (0.06 mol) of hydrazine in 50 ml of DMF and 50 ml of ethanol was stirred at reflux for 2 h. The resulting suspension was allowed to cool to ambient temperature and was then chilled in an ice bath and filtered. The solid was washed with a small volume of ethanol and allowed to air dry to give 1-hydrazono-1,3-dihydropyrrolo[3,2-f]quinolin-2-one as an orange solid (1.8 g, 73%): $^1$H NMR (DMSO-d$_6$): δ7.37 (d, J=8.8 Hz, 1H), 7.47 (dd, J=8.4, 4.2 Hz, 1H), 7.81 (d, J=8.8 Hz, $_1$H), 8.71 (dd, J=4.2, 1.6 Hz, 1H), 8.80 (d, J=8.4 Hz, 1H), 9.90 (br d, J=14.7 Hz, 1H), 10.89 (br d, J=14.7 Hz, 1H), 10.95 (br s, 1H); ESI-MS m/z 213 (M+H)$^+$. A solution 1.8 g (8.5 mmol) of 1-hydrazono-1,3-dihydropyrrolo[3,2-f]quinolin-2-one in 50 ml of freshly prepared 0.5 M sodium ethoxide solution was stirred at reflux for 3 h. The solution was diluted with 50 ml of water, neutralized with acetic acid, and concentrated on a rotary evaporator until cloudy. The solution was stored in a refrigerator overnight. The solid was filtered off, and the filtrate was extracted with three 80-ml portions of EtOAc. A solution of the solid in MeOH/EtOAc was combined with the extracts and passed through a short pad of silica gel, eluting with EtOAc. The solution was then concentrated to a small volume on a rotary evaporator, and the resulting suspension was diluted with an equal volume of ethanol, sonicated, and filtered to give 3-H-pyriolo[3,2-f]quinoline-2-one as a light green solid (0.52 g, 33%); $^1$H NMR (DMSO-$d_6$): δ3.80 (s, 2H), 7.35 (d, J=8.8 Hz, 1H), 7.44 (dd, J=8.4, 4.2 Hz, 1H), 7.88 (d, J=8.8 Hz, 1H), 8.08 (d, J=8.4 Hz, 1H), 8.70 (dd, J=4.2, 1.6 Hz, 1H), 10.57 (br s, 1H); APCI-MS m/z 183 (M−H)$^−$.

d) 3-H-Pyrrolo[3,2-f]quinoline-1,2-dione

To a 1 L flask was added sodium sulfate (0.6 mol) and water (100 mL) and the mixture was stirred until the solids dissolved. To this solution was added a solution of 6-aminoquinoline (0.033 mol) in 1N aqueous hydrochloric acid (50 mL) and ethanol (10 mL). The mixture was stirred and chloral (0.036 mol) was added. To the resulting solution was added a solution of hydroxylamine hydrochloride (0.108 mmol) in water (30 mL). This mixture was then heated to gentle reflux until all the solids dissolved and was then heated for a further 15 min. The flask was removed from the heat and the solution was poured onto ice (500 g) with stirring. The resulting solid was collected by filtration, washed with water and air dried to give N-quinolin-6-yl-2-hydroxyiminoacatamide (94%). To a 1L, 3 necked flask was added concentrated sulfuric acid (100 mL). The acid was stirred and heated to 100 C. N-Quinolin-6-yl-2-hydroxyiminoacatamide (45 mmol) was added slowly and the resulting solution was heated for 1 h. The reaction mixture was carefully poured onto ice/water (750 mL) and stirred for about 1 h. The solids were collected by filtration, washed with water and air dried to give the desired compound, (46%).

Example 2

1-[(Z)-(4-Diethylaminomethylanilino)metliylidene]-1,3-dihydro-2H-pyrrolo[3,2-f]quinoline-2-one

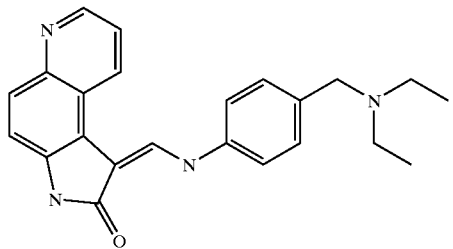

In a similar manner as described for Example 1(a), from 4-diethylaminomethylaniline was obtained the title compound as an orange-yellow solid, 8.6 mg. (22%). $^1$H NMR (DMSO-$d_6$): δ0.93–0.96 (m, 6H), 3.12–3.14 (m, 4H), 4.04–4.08 (m, 2H), 7.29–7.46 (m, 6H), 7.69 (d, J=8.6 Hz, 1H), 8.70 (d, J=2.9 Hz, 1H), 8.79 (d, J=7.9 Hz, 1H), 8.82 (d, J=12 Hz, 1H), 10.92 (s, 1H), 11.76 (d, J=12 Hz, 1H); APESI+MS m/z 373 (M+1)$^+$.

Example 3

1-[(Z)-(4-(N-Methyl)ethylaminomethylanilino) methylidene]-1,3-dihydro-2H-pyrrolo[3,2-f]quinoline-2-one

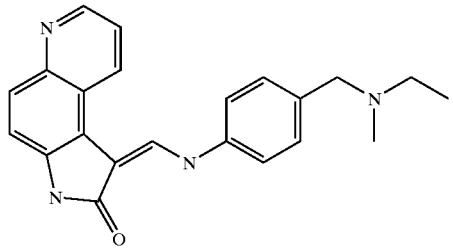

In a similar manner as described for Example 1(a), from 4-[N-(methyl)ethylaminometlhyl]aniline was obtained the title compound as a yellow solid, 13 mg. (35%). $^1$H NMR (DMSO-$d_6$): δ1.04 (t, 3H), 1.48 (m, 2H), 2.13 (bs, 3H), 2.40 (bs, 2H), 3.46 (bs, 2H), 7.33–7.51 (m, 6H), 7.74 (d, J=8.8 Hz, 1H), 8.74 (s, J=3.3 Hz, 1H), 8.82 (d, J=5.8 Hz, 1H), 8.85 (d, J=12 Hz, 1H), 10.95 (s, 1H), 11.81 (d, J=12 Hz, 1H); APESI+MS m/z 359 (M+1)$^+$.

Example 4

1-[(Z)-(4-(N-Methyl)propylaminomethylanilinio) methylidene]-1,3-dihydro-2H-pyrrolo[3,2-f]quinoline-2-one

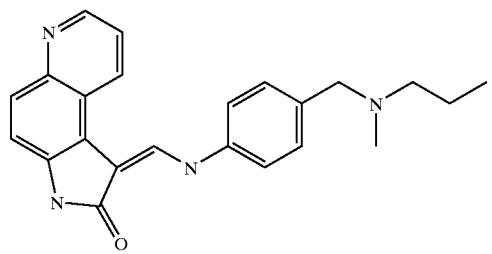

In a similar manner as described for Example 1(a), from 4-[N-(methyl)propylaminomethyl]aniline was obtained the title compound as a yellow-brown solid, 7.2 mg. (19%). $^1$H NMR (DMSO-$d_6$): δ 0.86 (t, 3H), 1.48 (m, 2H), 2.13 (bs, 3H), 2.29 (bs, 2H), 3.45 (bs, 2H), 7.35–7.51 (m, 6H), 7.74 (d, J=8.7 Hz, 1H), 8.74 (s, 1H), 8.83 (d,J=7.2 Hz, 1H), 8.86 (d,J=9.6 Hz, 1H), 10.95 (s, 1H), 11.81 (d,J=12 Hz, 1H); APESI+MS m/z 373 (M+1)$^+$.

Example 5

1-[(Z)-(4-(N-Methyl)-2-propylaminomethylanilino) metliylidene]-1,3-dihydro-2H-pyrrolo[3,2-f]quinoline-2-one

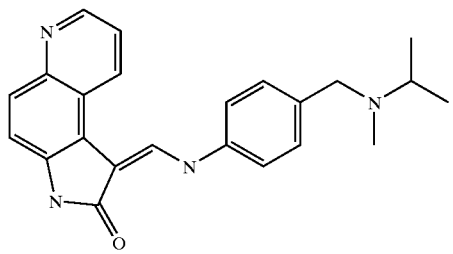

In a similar manner as described for Example 1(a), from 4-[N-(methyl)isopropylaminiomethyl]aniline was obtained the title compound as a yellow solid, 16 mg. (41%). $^1$H NMR (DMSO-d$_6$): δ1.02 (d, J=5.2 Hz, 6H), 2.07 (bs, 3H), 2.85 (m, 1H), 3.48 (bs, 2H), 7.36–7.49 (m, 6H), 7.74 (d, J=8.7 Hz, 1H), 8.74 (d, J=3.4 Hz, 1H), 8.82 (d, J=8.0 Hz, 1H), 8.86 (d, J=9.4 Hz, 1H), 10.95 (s, 1H), 11.81 (d, J=12 Hz, 1H); APESI+MS m/z 373 (M+1)$^+$.

Example 6

1-[(Z)-(4-(N-Methyl)-2-methylpropylaminomethylanilino)methylidene]-1,3-dihydro-2H-pyrrolo[3,2-f]quinoline-2-one

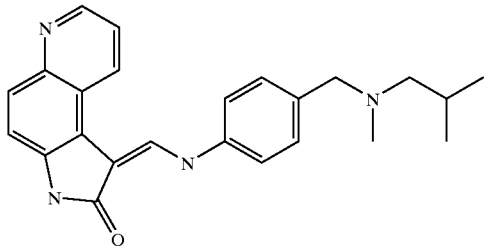

In a similar manner as described for Example 1(a), from 4-[N-(methyl)-2-methylpropylaminomethyl]aniline was obtained the title compound as a yellow-brown solid, 11 mg. (27%). $^1$H NMR (DMSO-d$_6$): δ 0.87 (d, J=6.5 Hz, 6H), 1.81 (m, 1H), 2.07 (d, J=7.1 Hz, 2H), 2.11 (s, 3H), 3.43 (s, 2H), 7.32–7.50 (m, 6H), 7.74 (d, J=8.7 Hz, 1H), 8.74 (d, J=3.1 Hz, 1H), 8.82 (d, J=5.7 Hz, 1H), 8.85 (d, J=12 Hz, 1H), 10.95 (s, 1H), 11.81 (d, J=12 Hz, 1H); APESI+MS m/z 387 (M+1)$^+$.

Example 7

1-[(Z)-(4-(N-Methyl)benzylaminomethylanilino)methylidene]-1,3-dihydro-2H-pyrrolo[3,2-f]quinoline-2-one

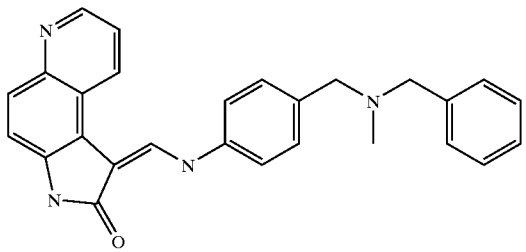

In a similar manner as described for Example 1(a), from 4-[N-(methyl)benzylaminomiiethyl]aniline was obtained the title compound as a yellow solid, 18 mg. (41%). $^1$H NMR (DMSO-d$_6$): δ 2.10 (s, 3H), 3.51 (s, 2H), 7.27–7.52 (m, 11H), 7.74 (d, J=8.7 Hz, 1H), 8.74 (s, J=4.0 Hz, 1H), 8.83 (d, J=6.0 Hz, 1H), 8.86 (d, J=12 Hz, 1H), 10.95 (s, 1H), 11.80 (d, J=12 Hz, 1H); APESI+MS m/z 421 (M+1)$^+$.

Example 8

1-[(Z)-(4-(N-Methyl)-2-hydroxyethylaminomethylanilino)methylidene]-1,3-dihydro-2H-pyrrolo[3,2-f]quinoline-2-one

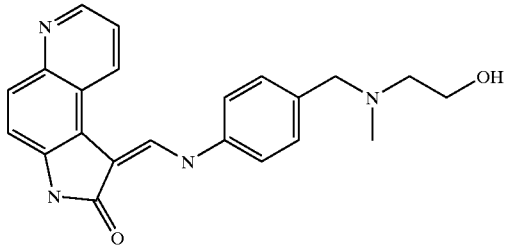

In a similar manner as described for Example 1(a), from 4-[N-(methyl)-2-hydroxyethylaminomethyl]aniline was obtained the title compound as a yellow solid, 10 mg. (26%). $^1$H NMR (DMSO-d$_6$): δ 2.17 (s, 3H), 2.44 (t, 2H), 3.49 (m, 2H), 4.40 (t, 1H), 7.33–7.50 (m, 6H), 7.74 (d. J=8.7 Hz, 1H), 8.73 (s, 1H), 8.83 (d, J=7.7 Hz, 1H), 8.86 (d, J=9.6 Hz, 1H), 10.95 (s, 1H), 11.81 (d, J=12 Hz, 1H); APESI+MS m/z 375 (M+1)$^+$.

Example 9

1-[(Z)-(4-(N-Methyl)-2-methoxyethylaminomethylanilino)methylidene]-1,3-dihydro-2H-pyrrolo[3,2-f]quinoline-2-one

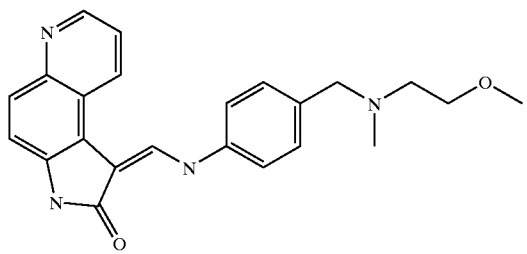

In a similar manner as described for Example 1(a), from 4-[N-(methyl)-2-methoxyethylamniniomiiethyl]aniline was obtained the title compound as a yellow solid, 18 mg. (41%). $^1$H NMR (DMSO-d$_6$): δ2.18 (bs, 3H), 2.54 (t, 2H), 3.24 (s, 3H), 3.46 (t, 2H), 3.50 (s, 2H), 7.32–7.51 (m, 6H), 7.74 (d, J=8.7 Hz, 1H), 8.73 (s, J=3.2 Hz, 1H), 8.82 (d, J=5.4 Hz, 1H), 8.85 (d,J=12 Hz, 1H), 10.95 (s, 1H), 11.81 (d,J=12 Hz, 1H); APESI+MS m/z 389 (M+1)$^+$.

Example 10

1-[(Z)-(4-(4-morpholinyl)methylanilino)methylidene]-1,3-dihydro-2H-pyrrolo[3,2-f]quinoline-2-one

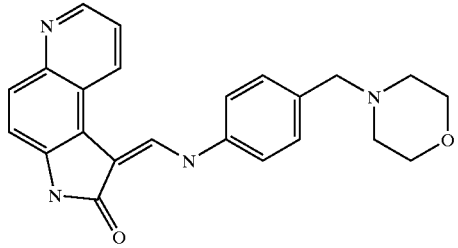

In a similar manner as described for Example 1(a), from 4-(4-morpholinyl)methylanilino was obtained the title compound as a yellow-brown solid, 19 mg (47%). $^1$H NMR (DMSO-d$_6$): δ 2.36 (bs, 4H), 3.46 (s, 2H), 3.58 (bs, 4H), 7.33–7.51 (m, 6H), 7.74 (d, J=8.7 Hz, 1H), 8.74 (d, J=3.0 Hz, 1H), 8.82 (d, J=4.3 Hz, 1H), 8.85 (d, J=12 Hz, 1H), 10.95 (s, 1H), 11.80 (d, J=12 Hz, 1H); APESI+MS m/z 387 (M+1)$^+$.

Example 11

1-[(Z)-(4-(1-piperidinyl)methylanilino)methylidene]-1,3-dihydro-2H-pyrraolo[3,2-f]quinoline-2-one

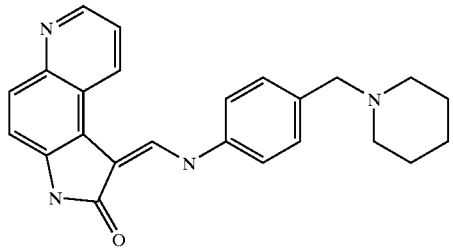

In a similar manner as described for Example 1(a), from 4-(1-piperidinyl)methylaniline was obtained the title compound as a khaki solid, 24 mg (60%). $^1$H NMR (DMSO-d$_6$): δ 1.40 (bs, 2H), 1.51 (bs, 4H), 2.33 (bs, 4H), 3.42 (bs, 2H), 7.32–7.49 (m, 6H), 7.74 (d, J=8.7 Hz, 1H), 8.73 (d, J=3.2 Hz, 1H), 8.82 (d, J=4.8 Hz, 1H), 8.86 (d, J=8.5 Hz, 1H), 10.95 (s, 1H), 11.80 (d, J=12 Hz, 1H); APESI+MS m/z 385 (M+1)$^+$.

Example 12

1-[(Z)-(4-(4-hydroxy-1-piperidinyl)methylanilino)methylidene]-1,3-dihydro-2H-pyrrolo[3,2-f]quinoline-2-one

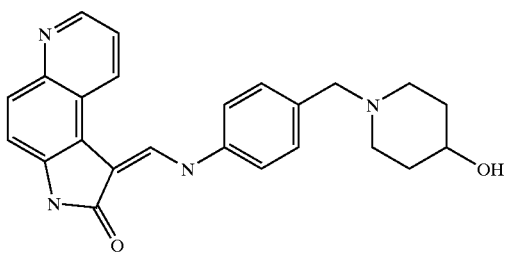

In a similar manner as described for Example 1(a), from 4-(4-hydroxy-1-piperidinyl)methylaniline was obtained the title compound as a yellow-orange solid, 2.6 mg. (6%). $^1$H NMR (DMSO-d$_6$): δ 1.40 (bs, 2H), 1.69 (bs, 2H), 2.02 (bs, 2H), 2.65 (bs, 2H), 3.43 (bs, 2H), 4.08 (m, 1H), 4.53 (bs, 1H), 7.34–7.49 (m, 6H), 7.74 (d, J=8.8 Hz, 1H), 8.73 (s, 1H), 8.82 (d, J=4.9 Hz, 1H), 8.85 (d, J=12 Hz, 1H), 10.95 (s, 1H), 11.80 (d, J=12 Hz, 1H); APESI+MS m/z 401 (M+1)$^+$.

Example 13

1-[(Z)-(4-(4-methyl-1-piperazinyl)methylanilino)methtylidene]-1,3-dihydro-2H-pyrrlo[3,2-f]quinoline-2-one

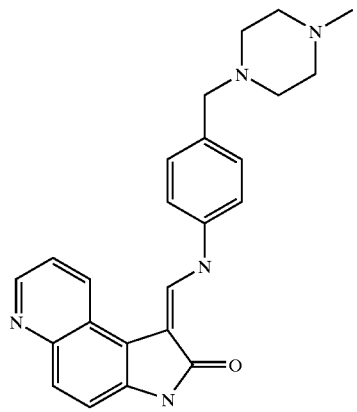

In a similar manner as described for Example 1(a), from 4-(4-methyl-1-piperazinyl)methylaniline was obtained the title compound as a dark maroon solid, 77 mg (78%) bis-hydrochloride salt. $^1$H NMR (DMSO-d$_6$): δ 2.79 (s, 4H), 3.3–3.5 (bs, 4H), 4.18 (bs, 2H), 7.6–7.7 (m, 3H), 7.70 (d, J=8.9 Hz, 1H), 7.83 (dd, J=4.8 Et 8.6 Hz, 1H), 8.00 (d, J=8.7 Hz, 1H), 8.63 (bs, 1H), 8.98 (d, J=3.4 Hz, 1H), 9.03 (s, 1H), 9.40 (d, 6.5 Hz, 1H), 9.75 (bs, 2H), 11.34 (s, 1H), 11.96 (d, J=12 Hz, 1H); APESI+MS m/z 400 (M+1)$^+$.

Example 14

1-[(Z)-(4-(1-imidazoyl)methylanilino)methylidene]-1,3-dihydro-2H-pyrrolo[3,2-f]quinoline-2-one

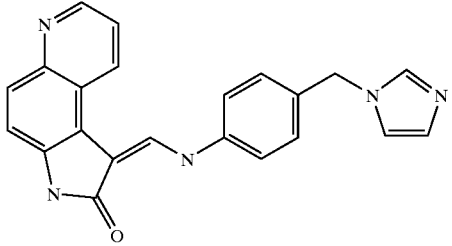

In a similar manner as described for Example 1(a), from 4-(1-imidazoyl)methylaniline was obtained the title compound as a rust solid, 28 mg. (73%). $^1$H NMR (DMSO-d$_6$): δ5.18 (s, 2H), 6.91 (s, 1H), 7.21 (s, 1H), 7.32–7.54 (m, 6H), 7.73 (s, 1H), 7.76 (d, J=4.1 Hz, 1H), 8.74 (d, J=3.6 Hz, 1H), 8.80 (s, 1H), 8.84 (d, J=4.5 Hz, 1H), 10.96 (s, 1H), 11.80 (d, J=12 Hz, 1H); APESI+MS m/z 368 (M+1)$^+$.

Example 15

1-[(Z)-(4-(N-Methyl)-(1-methyl-4-piperidinyl)aminomethylanilino)methylidene]-1,3-dihydro-2H-pyrrolo[3,2-f]quinoline-2-one

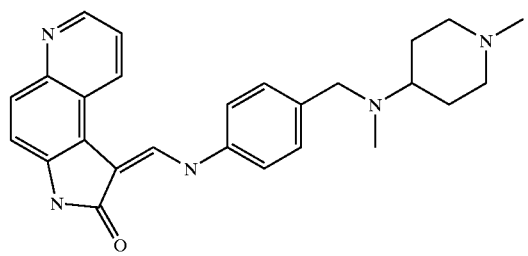

In a similar manner as described for Example 1(a), from 4-(N-methyl)-(1-methyl-4-piperidinyl)aminomethylaniline was obtained the title compound as a rust solid, 7.7 mg. (17%). $^1$H NMR (DMSO-d$_6$): δ 1.55–1.85 (m, 4H), 2.11 (m, 4H), 2.54 (s, 3H), 2.84 (m, 1H), 3.50 (s, 2H), 3.54 (s, 3H), 4.40 (t, 1H), 7.32–7.49 (m, 6H), 7.74 (d, J=8.7 Hz, 1H), 8.73 (s, 1H), 8.84–8.87 (m, 2H), 10.95 (s, 1H), 11.81 (d, J=12 Hz, 1H); APESI+MS m/z 428 (M+1)$^+$.

Biological Data

The compounds of the present invention have valuable pharmacologic properties. Different compounds from this class are particularly effective at inhibiting CDK2 and/or CDK4 enzymes at concentrations, which range from 0.0001 to 1 μM and additionally show specificity relative to other kinases. Representative data is shown in Table 1 following. Substrate phosphorylation assays were carried out as follows:

CDK4

Cyclin D1 and cyclin-dependent kinase 4 were expressed utilizing a baculovirus expression system. The catalytic activity of CDK4 protein was assayed by measuring the phosphorylation of Rb protein. A truncated Rb protein (residues 773–928 of the native retinoblastoma protein, fused to glutathione S-transferase to facilitate purification) was used as the phosphoryl acceptor. The assay conditions were 100 mM HEPES (N-[2-hydroxyethyl]piperzine-N'-[2-ethanesulfonic acid]), pH 7.5, 0.5 μM GST-Rb protein, 1 μCi/mL [$^{33}$P]-ATP (1 nM-20 μM), 5–20 mM MgCl$_2$, 2.5 mM EDTA, 1 mM dithiothieitol, 0.2 mg/mL bovine serum albumin, 2% (v/v) dimethyl sulfoxide (DMSO), CDK4 enzyme (5–50 nM) in a final volume of 50 μL. Reactions were incubated for time periods of 10–60 min at 30° C. and terminated by the addition of 50 μL quench (1 mM ATP/100 mM EDTA, pH 7.0). Detection of protein phosphorylation was accomplished by scintillation counting following collection of protein in 96 well plates coated with Glitathione or trapping of protein onto phosphocellulose filters. Counts detected by these methodologies minus the appropriate background were assumed to be proportional to the reaction initial rates. IC$_{50}$ values were determined by measuring enzyme activity in the presence of different inhibitor concentrations (0.1 nM to 50 μM). IC$_{50}$s were determined by a least squares fit to the equation CPM=Vmax*(1−([I]/(K+[I])))+nsb, or pIC50s were determined by a fit to the equation CPM=nsb+(Vmax−nsb)/(1+(x/10$^x$−pIC50)), where nsb are the background counts.

CDK2

Cyclin dependent protein kinase 2 assays utilized the peptide Biotin-aminohexyl-ARRPMSPKKKA-NH$_2$ as phosphoryl group acceptor. CDK2 was expressed utilizing a baculovirus expression system and was partially purified to comprise 20–80% of total protein, with no detectable competing reactions present. Typically, assays were performed by incubating enzyme (0.2–10 nM), with and without inhibitor, peptide substrate (1–10 nM), [g-$^{32}$P]ATP (1–20 nM), and 10–20 mM Mg$^{2+}$ for periods of time generally within the range 10–120 minutes. Reactions were terminated with 0.2–2 volumes of either 20% acetic acid or 50–100 mM EDTA buffered to pH 7 (substrate consumption <20%). The buffer employed in enzyme assay was 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=Vmax*(1−([I]/(K+[I])))+nsb, or −pIC50s were determined by a fit to the equation CPM=nsb+(Vmax−nsb)/(1+(x/10$^x$−pIC50)), where nsb are the background counts. filters and washed four times with 75 mM phosphoric acid. Radioactivity was determined by liquid scintillation counting.

Anti-Proliferation Cell-Based Assay

The anti-proliferative activity of compounds was determined measuring the rate of DNA synthesis by bromodeoxyuridine (BrdU) incorporation into cellular DNA. The amount of BrdU in cellular DNA was detected using an anti-BrdU antibody in an ELISA format to allow for rapid throughput. Log-phase growing human tumor cells either containing functional Rb (U2OS, MDA-MB-231) or lacking functional Rb protein (SaOs-2, MDA-MB-468) were plated in medium into 96-well plates (1–6×10$^3$ cells/100 μL medium/well) and allowed to incubate overnight ~30 hr. Compounds (concentration range of 0.046–100 μM) were diluted in medium (final DMSO (v/v) 0.8%), added to wells containing cells, and incubated for 18 hr at 37° C. BrdU (100 μM) was added and incubated for 4 hr. Cells were rinsed with PBS and DNA was denatured by addition of fixation/denaturation solution. Anti-BrdU antibody conjugated to horseradish peroxidase in 1% BSA was added for 2 hr at room temperature. Cells were washed, the chemiluminescence reagent was added, and plates were read in luminometer. Typical IC$_{50}$ values for the compounds of the present invention when tested in the anti-proliferation assay were in the range of 0.05–10 μM.

TABLE 1

| Example # | CDK4 inhibition | CDK2 inhibition | Anti-proliferative activity |
|---|---|---|---|
| 1 | +++ | ++ | ++ |
| 6 | +++ | ++ | +++ |
| 10 | +++ | +++ | ++ |

Scale
+++ = <0.1 μM
++ = <1.0 μM
++ = <10 μM

We claim:
1. A compound of Formula I

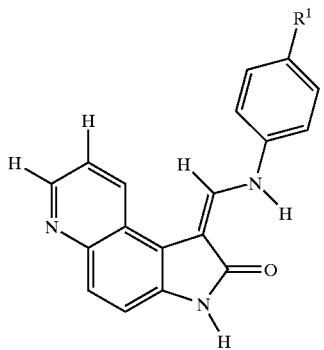

(I)

or a salt, solvate, or a physiologically functional derivative thereof:
wherein:
$R^1$ is $(CR^4R^5)_n NR^2R^3$;
n is 1 or 2;
$R^2$ and $R^3$ are independently hydrogen, $C_{1-6}$ alkyl, $C_{1-6}$ alkenyl, $C_{1-6}$ alkoxy-$C_{1-6}$ alkyl, cycloalkyl, heterocyclyl, benzyl, phenyl, napthyl, heteroaryl, heteroaryl-$C_{1-6}$ alkyl, or $R^2$ and $R^3$ together with the nitrogen to which they are bound form a 5 or 6 membered heterocyclic ring or a 5 to 7 membered heteroaryl ring, both rings optionally containing 1 or 2 additional oxygen, sulfur, $S(O)_m$, or nitrogen atoms, said additional nitrogen atom being optionally substituted by a $C_{1-6}$ alkyl or aryl group;
m is 0, 1, or 2;
$R^4$ and $R^5$ are independently hydrogen or $C_{1-6}$ alkyl; and
wherein any of said $C_{1-6}$ alkyl, $C_{1-6}$ alkenyl, $C_{1-6}$ alkyl-$C_{1-6}$ alkoxy, cycloalkyl, heterocyclyl, benzyl, phenyl, nalthyl, heteroaryl and heteroaryl-$C_{1-6}$ alkyl groups can be optionally substituted with up to three members selected from a group consisting of halogen, hydroxyl, $CF_3$ and $N(CH_3)_2$.

2. A compound as claimed in claim 1, wherein $R^2$ and $R^3$ are $C_{1-6}$ alkyl.

3. A compound as claimed in claim 1, wherein $R^2$ is methyl and $R^3$ is selected from the group consisting of ethyl, propyl, iso-propyl, isobutyl, hydroxyethyl, methoxyethyl, benzyl, and methylpiperidinyl.

4. A compound as claimed in claim 1, wherein $R^2$ and $R^3$ together with the nitrogen to which they are bound, form a heterocyclic ring optionally containing 1 or 2 additional heteroatoms selected from nitrogen, nitrogen substituted with a $C_{1-6}$ alkyl group, O, or $S(O)_m$.

5. A compound as claimed in claim 4, wherein said ring is a piperidine, morpholine or piperazine ring, wherein when $R^2$ and $R^3$ form a piperazine ring N is substituted by a methyl group.

6. A compound as claimed in claim 1, wherein $R^2$ and $R^3$ together with the nitrogen to which they are bound, form a heteroaryl ring optionally containing 1 or 2 additional heteroatoms selected from nitrogen, nitrogen substituted with a $C_{1-6}$ alkyl group, O, or $S(O)_m$.

7. A compound as claimed in claim 6, wherein said ring is an imidazole ring.

8. A compound as claimed in claim 1, wherein $R^4$ and $R^5$ are each hydrogen.

9. A compound as claimed in claim 1, wherein $R^2$ and $R^3$ are each $C_{1-6}$ alkyl and $R^4$ and $R^5$ are independently hydrogen or methyl.

10. A compound as claimed in claim 1, wherein $R^2$ is methyl; $R^3$ is ethyl, propyl, iso-propyl, isobutyl, hydroxyethyl, methoxyethyl, benzyl, or methylpiperidinyl; and $R^4$ and $R^5$ are each hydrogen.

11. A compound as claimed in claim 1, wherein $R^2$ and $R^3$, together with the nitrogen to which they are bound, form a heterocyclic ring optionally containing an additional nitrogen or $C_{1-6}$ alkyl substituted nitrogen, oxygen, or $S(O)_m$ and $R^4$ and $R^5$ are independently hydrogen or methyl.

12. A compound as claimed in claim 11, wherein said ring is a piperidine, morpholine or piperazine ring and $R^4$ and $R^5$ are hydrogen.

13. A compound as claimed in claim 1, wherein $R^2$ and $R^3$ together with the nitrogen to which they are bound form a piperazine ring, wherein the additional nitrogen is substituted by a methyl group, and $R^4$ and $R^5$ are hydrogen.

14. A compound as claimed in claim 1, wherein $R^2$ and $R^3$, together with the nitrogen to which they are bound, form a heteroaryl ring optionally containing an additional nitrogen or $C_{1-6}$ alkyl substituted nitrogen, oxygen, or $S(O)_m$ and $R^4$ and $R^5$ are independently hydrogen or methyl.

15. A compound as claimed in claim 14, wherein said ring is an imidazole ring and $R^4$ and $R^5$ are hydrogen.

16. A compound as claimed in claim 1, selected from the group consisting of:
1-[(Z)-(4-Dimethylaminomethylanilino)methylidene]-1,3-dihydro-2H-pyrrolo[3,2-f]quinoline-2-one;
1-[(Z)-(4-Diethylaminomethylanilino)methylidene]-1,3-dihydro-2H-pyriolo[3,2-f]quinoline-2-one;
1-[(Z)-(4-(N-Methyl)ethylaminomethylanilino) methylidene]-1,3-dihydro-2H-pyrrolo[3,2-f]quinoline-2-one;
1-[(Z)-(4-(N-Methyl)propylaminomethylanilino) methylidene]-1,3-dihydro-2H-pyrrolo[3,2-f]quinoline-2-one;
1-[(Z)-(4-(N-Methyl)-2-propylaminomethylanilino) methylidene]-1,3-dihydro-2H-pyrrolo[3,2-f]quinoline-2-one;
1-[(Z)-(4-(N-Methyl)-2-methylpropylaminomethyl-anilino)methylidene]-1,3-dihydro-2H-pyrrolo[3,2-f]quinoline-2-one;
1-[(Z)-(4-(N-Methyl)benzylaminomethylanilino) methylidene]-1,3-dihydro-2H-pyrrolo[3,2-f]quinoline-2-one;
1-[(Z)-(4-(N-Methyl)-2-hydroxyethylaminomethyl-anilino)methylidene]-1,3-dihydro-2H-pyrrolo[3,2-f]quinoline-2-one;
1-[(Z)-(4-(N-Methyl)-2-methoxyethylaminomethyl-anilino)methylidene]-1,3-2H-pyrrolo[3,2-f]quinoline-2-one;
1-[(Z)-(4-(4-morpholinyl)methylanilino)methylidene]-1,3-dihydro-2H-pyrrolo[3,2-f]quinoline-2-one;
1-[(Z)-(4-(1-piperidinyl)methylanilino)methylidene]-1,3-dihydro-2H-pyirolo[3,2-f]quinoline-2-one;
1-[(Z)-(4-(4-hydroxy-1-piperidinyl)methylanilino) methylidene]-1,3-dihydro-2H-pyrrolo[3,2-f]quinoline-2-one;
1-[(Z)-(4-(4-methyl-1-piperazinyl)methylanilino) methylidene]-1,3-dihydro-2H-pyrrolo[3,2-f]quinoline-2-one;
1-[(Z)-(4-(1-imidazoyl)methylanilino)methylidene]-1,3-dihydro-2H-pyrrolo[3,2-f]quinoline-2-one;
1-[(Z)-(4-(N-Methyl)-(1-methyl-4-piperidinyl) aminomethylanilino)methylidene]-1,3-dihydro-2H-pyrrolo[3,2-f]quinoline-2-one; and salts, solvates, or physiologically functional derivatives thereof.

17. A pharmaceutical composition, comprising: a therapeutically effective amount of a compound as claimed in claim 1, or a salt, solvate, or a physiologically functional derivative thereof and one or more of pharmaceutically acceptable carriers, diluents and excipients.

18. A method of treating a disorder in a mammal, said disorder being mediated by inappropriate CDK4 activity, comprising: administering to said mammal a therapeutically effective amount of a compound as claimed in claim 1, or a salt, solvate, or a physiologically functional derivative thereof.

19. A method of treating a susceptible cancer in a mammal, comprising: administering to said mammal a therapeutically effective amount of a compound as claimed in claim 1, or a salt, solvate, or a physiologically functional derivative thereof.

20. A method of treating a disorder in a mammal, said disorder being mediated by inappropriate cyclin dependent kinase activity, comprising: administering to said mammal a therapeutically effective amount of a compound as claimed in claim 1, or a salt, solvate or physiologically functional derivative thereof.

* * * * *